(12) United States Patent
Powers

(10) Patent No.: US 6,410,726 B1
(45) Date of Patent: Jun. 25, 2002

(54) ARYLSULFONIC ACID SALTS OF PYRIMIDINE-BASED ANTIVIRAL

(75) Inventor: Jay P. Powers, Pacifica, CA (US)

(73) Assignee: Tularik Inc., So. San Francisco, CA (US)

( * ) Notice: Subject to any disclaimer, the term of this patent is extended or adjusted under 35 U.S.C. 154(b) by 0 days.

(21) Appl. No.: 09/757,291

(22) Filed: Jan. 8, 2001

Related U.S. Application Data

(60) Provisional application No. 60/176,000, filed on Jan. 12, 2000.

(51) Int. Cl.⁷ .................. C07D 413/04; A61K 31/535
(52) U.S. Cl. .................. 544/122; 544/324; 514/273; 514/235.8
(58) Field of Search ................ 544/122, 324; 514/273, 235.8

(56) References Cited

U.S. PATENT DOCUMENTS

| | | | |
|---|---|---|---|
| 3,178,432 A | | 4/1965 | Druey et al. |
| 4,696,928 A | * | 9/1987 | Ellames et al. ............ 514/250 |
| 4,698,340 A | | 10/1987 | Takaya et al. |
| 4,788,195 A | | 11/1988 | Torley et al. |
| 4,929,726 A | | 5/1990 | Strekowski et al. |
| 4,983,608 A | | 1/1991 | Effland et al. |
| 4,987,146 A | | 1/1991 | Rohde et al. |
| 5,147,876 A | | 9/1992 | Mizuchi et al. |
| 5,223,505 A | * | 6/1993 | Hargreaves et al. ........ 514/275 |
| 5,304,647 A | | 4/1994 | Strekowski et al. |
| 5,525,724 A | | 6/1996 | Hunds |
| 5,602,252 A | * | 2/1997 | Davey et al. ............... 544/115 |
| 5,854,419 A | * | 12/1998 | Davey et al. ............... 544/115 |
| 6,200,977 B1 | * | 3/2001 | Cushing et al. ........ 514/252.14 |

FOREIGN PATENT DOCUMENTS

| | | |
|---|---|---|
| DE | 23 41 925 A1 | 3/1975 |
| DE | 143 615 | 9/1980 |
| EP | 429149 | 5/1991 |
| EP | 0 640 599 | 3/1995 |
| EP | 0 806 418 | 11/1997 |
| WO | WO 98 23597 A1 | 6/1998 |
| WO | WO 99/41253 | 8/1999 |

OTHER PUBLICATIONS

Berge et al. J. of Pharmaceutial Science, 1977, 66, 1–19.*

* cited by examiner

Primary Examiner—Floyd D. Higel
Assistant Examiner—Kamal Saeed
(74) Attorney, Agent, or Firm—Townsend and Townsend and Crew LLP

(57) ABSTRACT

Salts of pyrimidine derivatives are provided having the formula:

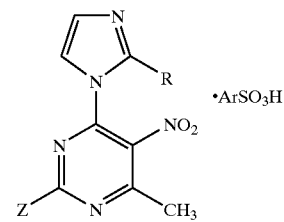

wherein R represents hydrogen, methyl or ethyl; Z represents a substituted or unsubstituted 1-piperidinyl, a substituted or unsubstituted 4-morpholinyl, or a substituted or unsubstituted 1-pyrrolidinyl; and Ar represents a substituted or unsubstituted phenyl or a substituted or unsubstituted naphthyl. These salts are particularly useful as antiviral agents (e.g., to treat CMV infections).

28 Claims, 2 Drawing Sheets

ARYLSULFONIC ACID SALTS OF PYRIMIDINE-BASED ANTIVIRAL

CROSS-REFERENCES TO RELATED APPLICATIONS

This application is related to U.S. Ser. No. 09/249,641, filed Feb. 12, 1999, the contents of which are incorporated by reference. This Application claims benefit to provisional Application 60/176,001 Jan. 12, 2000.

STATEMENT AS TO RIGHTS TO INVENTIONS MADE UNDER FEDERALLY SPONSORED RESEARCH AND DEVELOPMENT

Not applicable

FIELD OF THE INVENTION

The field of the invention is in salts of substituted pyrimidine compounds and their use as pharmacologically active agents capable of suppressing and inhibiting viruses (e.g., herpes viruses). The subject compounds and compositions are particularly useful in treating and suppressing human Cytomegalovirus.

BACKGROUND OF THE INVENTION

Cytomegalovirus (CMV) is a member of the herpes virus family. Other well-known members of the herpes virus family include, for example, herpes simplex virus, types I and II, Epstein-Barr virus and varicella zoster virus. These viruses are related taxonomically, but each manifests in a clinically distinct manner. In the case of CMV, medical conditions arising from congenital infection include jaundice, respiratory distress and convulsive seizures which may result in mental retardation, neurologic disability or death. Infection in adults is frequently asymptomatic, but may manifest as mononucleosis, hepatitis, pneumonitis or retinitis, particularly in immunocompromised patients such as AIDS sufferers, chemotherapy patients, and organ transplant patients undergoing tissue rejection therapy.

A variety of drugs have been developed to treat herpes virus infections, including naturally occurring proteins and synthetic nucleoside analogs. For example, the natural antiviral protein interferon has been used in the treatment of herpes virus infections, as have the nucleoside analogs cytosine-arabinoside, adenine-arabinoside, iodoxyuridine and acyclovir, which is presently the treatment of choice for herpes simplex type II infection.

Unfortunately, drugs such as acyclovir that have proven sufficiently effective to treat infection by certain herpes viruses are not sufficiently effective to treat CMV. Additionally, drugs currently used to treat CMV infection, such as 9-((1,3-dihydroxy-2-propoxy)methyl)guanidine (ganciclovir, DHPG) and phosphonoformic acid (foscarnet), lack the acceptable side effect and safety profiles of the drugs approved for treatment of other herpes viruses. Moreover, such drugs are ineffective to treat certain strains of CMV that have acquired drug resistance. Thus, despite advances in the development of anti-herpes virus drugs, there remains a need for therapeutic agents effective in treating CMV infection with an increased safety margin. Recently, PCT US99/03136 described the use of pyrimidine derivatives for the treatment of antiviral infections.

The present invention provides salts of certain pyrimidine derivatives which are surprisingly effective in treating viral infection and which have properties suitable for clinical use.

SUMMARY OF THE INVENTION

In one aspect, the present invention provides compounds having the formula:

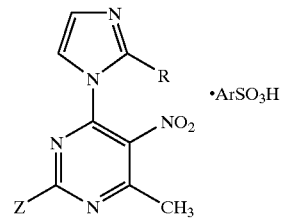

In this formula, R represents hydrogen, methyl or ethyl; Z represents a substituted or unsubstituted 1-piperidinyl, a substituted or unsubstituted 4-morpholinyl, or a substituted or unsubstituted 1-pyrrolidinyl; and Ar represents a substituted or unsubstituted phenyl or a substituted or unsubstituted naphthyl.

The compounds of the present invention are useful in therapeutic as well as prophylactic and diagnostic applications. Accordingly, the present invention provides compositions containing the above compounds and pharmaceutically acceptable excipients or diagnostically acceptable excipients. The invention further provides methods of inhibiting or suppressing certain viruses, and methods of treating individuals infected with such viruses, particularly CMV. In addition to treatments for existing conditions, the present invention also provides methods for prophylactic treatments to prevent the onset of viral infection in patients undergoing, for example, organ transplants.

Other objects, features and advantages of the present invention will become apparent to those skilled in the art from the following description and claims.

DESCRIPTION OF THE INVENTION

Abbreviations and Definitions

Figure 1:
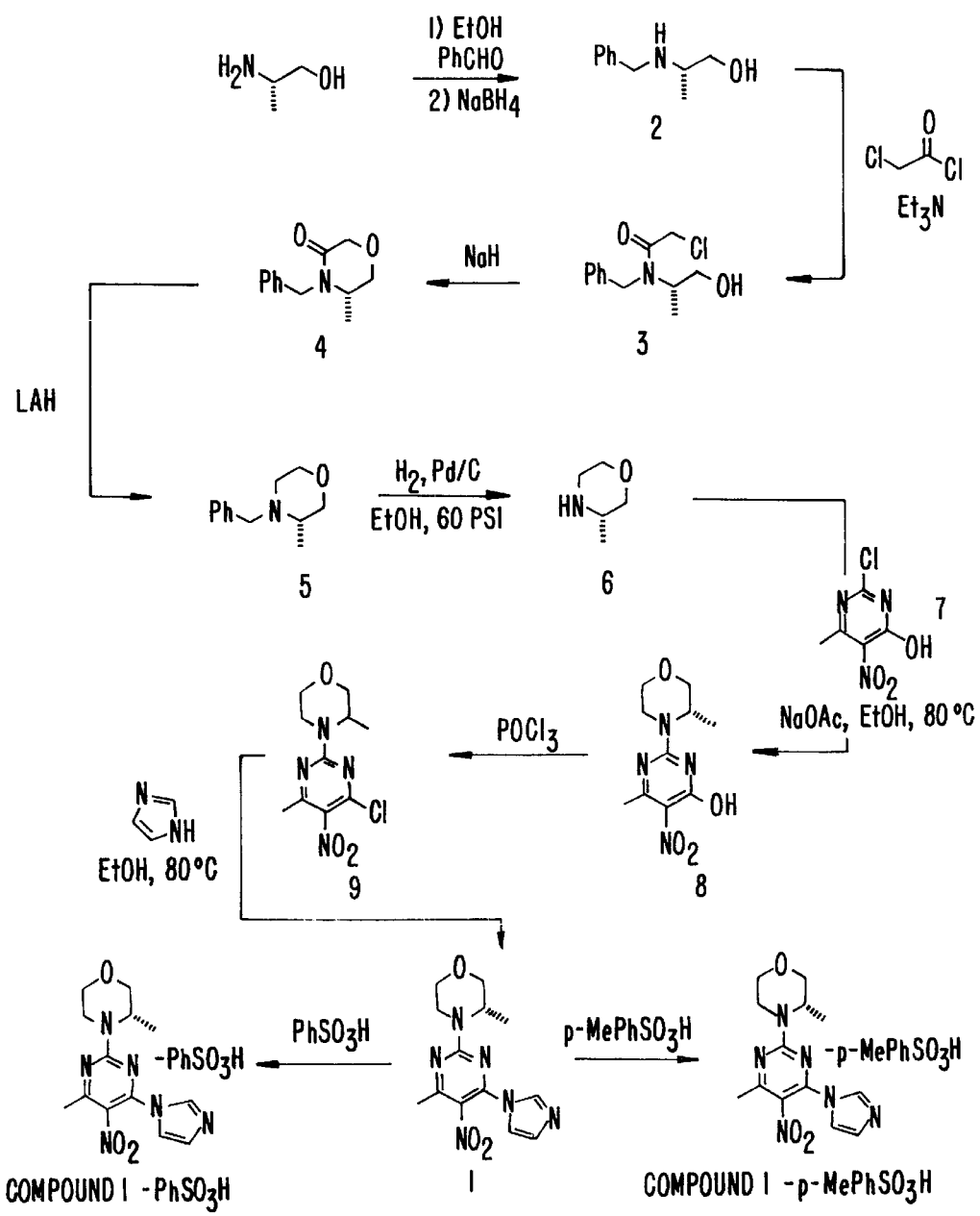
FIG. 1 provides a synthesis scheme for the preparation of salts of compound 1.

The term "alkyl," by itself or as part of another substituent, means, unless otherwise stated, a straight or branched chain or cyclic hydrocarbon radical or combinations thereof, which may be fully saturated, mono- or polyunsaturated and can include di- and multi-radicals, having the number of carbon atoms designated (i.e. C1–C10 means one to ten carbons). Examples of saturated hydrocarbon radicals include straight or branched chain groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. Other saturated hydrocarbon radicals include cyclopropylmethyl, cyclohexylmethyl and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined below as heteroalkyl, alkylene, heteroalkylene, cycloalkyl and heterocycloalkyl. Typically, an alkyl group will have from 1 to 24 carbon atoms, with those groups having 10 or fewer carbon atoms being preferred in the present invention. The term "alkylene" by itself or as part of another substituent means a divalent radical derived from an alkane, as exemplified by —$CH_2CH_2CH_2CH_2$—. A "lower alkyl" or "lower alkylene" is a shorter chain alkyl or alkylene group, generally having eight or fewer carbon atoms. Unless otherwise indicated, the alkyl groups can be unsubstituted or substituted by the substituents indicated below.

The term "heteroalkyl," by itself or in combination with another term, means, unless otherwise stated, a stable straight or branched chain radical consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—.

The terms "cycloalkyl" and "heterocycloalkyl", by themselves or in combination with other terms, represent, unless otherwise stated, cyclic versions of "alkyl" and "heteroalkyl", respectively. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl. More particularly, the term "fluoroalkyl" also includes perfluoroalkyl, in which each hydrogen present in an alkyl group has been replaced by a fluorine.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O and S, wherein the nitrogen and sulfur atoms are optionally oxidized, and the nitrogen atom(s) are optionally quaternized. Non-limiting examples of aryl groups include phenyl, 1-naphthyl, 2-naphthyl, biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below.

As used herein, the term "bicyclic fused aryl-cycloalkyl" refers to those groups in which an aryl ring (or rings) is fused to a cycloalkyl group (including cycloheteroalkyl groups). The group can be attached to the remainder of the molecule through either an available valence on the aryl portion of the group, or an available valence on the cycloalkyl portion of the group. Examples of such bicyclic fused aryl-cycloalkyl groups are: indanyl, benzotetrahydrofuranyl, benzotetrahydropyranyl and 1,2,3,4-tetrahydronaphthyl.

Each of the above terms (e.g., "alkyl" and "aryl" and "bicyclic fused aryl-cycloalkyl") will typically include both substituted and unsubstituted forms of the indicated radical. Preferred substituents for each type of radical are provided below. In the case of radicals containing both aryl (including heteroaryl) and alkyl (including, for example, heteroalkyl, cycloalkyl, and cycloheteroalkyl) portions, each of the portions can be substituted as indicated.

Substituents for the alkyl groups (including those groups often referred to as alkenyl, heteroalkyl, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halo, —SiR'R"R'", —OC(O)R', —CO$_2$R', —CONR'R", —OC(O)NR'R", —NR"C(O)R', —NR"—C(O)—OR', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2N+1), where N is the total number of carbon atoms in such radical. R', R" and R'" each independently refer to a hydrogen or C1–C10 alkyl group. Preferably, a substituted alkyl group will have from one to six independently selected substituents. More preferably, a substituted alkyl group will have from one to four independently selected substituents. Nevertheless, certain substituted alkyl groups (e.g., perfluoroalkyl) will have a full 2N+1 substituents (where N is the number of carbon atoms in a saturated alkyl group). Examples of substituted alkyl groups include: —C(O)—$CH_3$, —C(O)$CH_2$OH, —$CH_2$—CH($CO_2$H)—$NH_2$ and —Si($CH_3$)$_2$—$CH_2$—C(O)—$NH_2$.

Similarly, substituents for the aryl groups are varied and are selected from: -halo, —OR', —OC(O)R', —NR'R", —SR', —R', —CN, —NO$_2$, —CO$_2$R', —CONR'R", —OC(O)NR'R", —NR"C(O)R', —NR"—C(O)—OR', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C1–C4)alkoxy, and perfluoro(C1–C4)alkyl, in a number ranging from zero to the total number of open valences on the aromatic ring system; and where R' and R" are independently selected from hydrogen, (C1–C8)alkyl, aryl, aryl-(C1–C4)alkyl, and aryloxy-(C1–C4)alkyl.

Two of the substituents on adjacent atoms of the aryl ring may optionally be replaced with a substituent of the formula —T—C(O)—($CH_2$)$_s$—U—, wherein T and U are independently —NH—, —O—, —$CH_2$— or a single bond, and the subscript s is an integer of from 0 to 2. Alternatively, two of the substituents on adjacent atoms of the aryl ring may optionally be replaced with a substituent of the formula —A—($CH_2$)$_p$—B—, wherein A and B are independently —$CH_2$—, —O—, —NH—, —S—, —S(O)—, —S(O)$_2$—, —S(O)₂NR'— or a single bond, and p is an integer of from 1 to 3. One or more of the single bonds of the new ring so formed may optionally be replaced with a double bond. Alternatively, two of the substituents on adjacent atoms of the aryl ring may optionally be replaced with a substituent of the formula —(CH₂)$_q$—Z—(CH₂)$_r$—, where q and r are independently integers of from 1 to 3, and Z is —O—, —NR'—, —S—, —S(O)—, —S(O)₂—, or —S(O)₂NR'—. The substituent R' in —NR'— and —S(O)₂NR'— is selected from hydrogen or (C1–C6)alkyl.

As used herein, the term "heteroatom" is meant to include oxygen (O), nitrogen (N), sulfur (S) and silicon (Si).

Certain compounds of the present invention can exist in unsolvated forms as well as solvated forms, including hydrated forms. In general, the solvated forms are equivalent to unsolvated forms and are intended to be encompassed within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General

A variety of pyrimidine-based antiviral compounds have been described in co-pending U.S. Ser. No. 09/249,641, filed Feb. 12, 1999 and in PCT application US99/03136. The development of a pyrimidine-based antiviral agent (such as those described hereinbelow) for clinical use required the identification of a salt form with optimal physical and chemical properties. The most critical properties included crystallinity, aqueous solubility, light stability and thermal stability. As noted above, applications U.S. Ser. No. 09/249,641 and PCT US99/03136 describe pyrimidine derivatives both as free bases and as their pharmaceutically acceptable salts. Among the salts listed for this group of compounds are hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. There is no teaching or suggestion that the benzenesulfonate or p-tolylsulfonate are superior salt forms of the pyrimidine derivatives described herein. Interestingly, within the family of compounds provided in the above-noted applications, certain free base compounds of formula I below (neutral forms, without any acid addition salt formation) were found to have aqueous solubilities that were too low for acceptable oral bioavailability (e.g., compound 1 exhibits an aqueous solubility of 1.68 mg/mL).

In order to prepare suitable formulations of the compounds of formula I below, standard salt formation methods were pursued. However, HCl salts which have proven effective for a variety of related pyrimidine derivatives in earlier work were not effective for certain compounds of formula I, below. Surprisingly, initial attempts at HCl salt formation resulted only in oils which could not be crystallized or made into solids which would be pharmaceutically useful. A variety of other acids were investigated as shown in Table 1 (see Example 2). These acids represent most of the pharmaceutical salts used today.

Additionally, compound 1 was found to have an unusually low pKa of the free base (pKa=4.09) and weaker acids (pKa>2.0) were not strong enough acids to protonate the free base and form salts with compound 1. Thus, carboxylate salts such as acetate, citrate, etc. were ineffective. Moreover, strong acids which could protonate the free base of compound 1, even with its low pKa, led to decomposition of compound 1 by hydrolysis of the imidazole. Still further, all acids with pKa's<−1.2 were not suitable for salt formation due to decomposition of the free base (compound 1). This family of strong acids includes all of the mineral acids such as hydrochloric acid, sulfuric acid and nitric acid, as well as the commonly used methanesulfonic acid.

Only a very narrow range of acid pKa values which would lead to suitable salt formation and impart properties necessary for acceptable formulation and oral bioavailability. Quite surprisingly (based on efforts with other pyrimidine derivatives and their salts), the benzene and toluenesulfonic acid salts give significantly improved oral bioavailability over the free base, which will allows a lower dosage to be used and provides an improved safety profile.

Embodiments of the Invention

Compounds

In view of the above discoveries, the present invention provides in one aspect, certain salts of pyrimidine derivatives having pharmacologic profiles which make them surprisingly effective and advantageous for clinical use.

The compounds are represented by the formula:

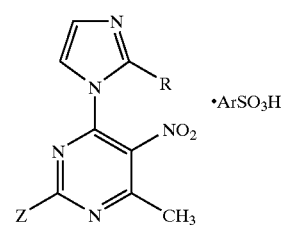

I in which R represents hydrogen, methyl or ethyl; Z represents a substituted or unsubstituted 1-piperidinyl, a substituted or unsubstituted 4-morpholinyl, or a substituted or unsubstituted 1-pyrrolidinyl; and Ar represents a substituted or unsubstituted phenyl or a substituted or unsubstituted naphthyl.

In one group of preferred embodiments, R is hydrogen. More preferably, R is hydrogen and Z is a substituted or unsubstituted 4-morpholinyl group. Still more preferably, R is hydrogen, Z is a substituted or unsubstituted 4-morpholinyl group and Ar is substituted or unsubstituted phenyl. Preferred substituents for the 4-morpholinyl group are (C₁–C₄)alkyl groups (e.g., methyl, ethyl, propyl, isopropyl, 1-butyl, 2-butyl, 2-methyl-1-propyl, 1,1-dimethyl-1-ethyl). Particularly preferred groups for Ar are phenyl and paratolyl.

In the most preferred embodiments, the compound has the formula:

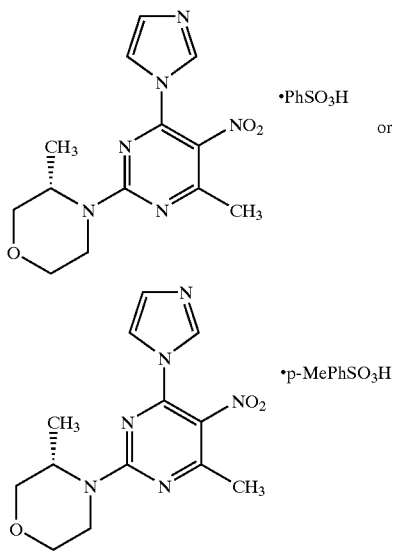

Compositions

In another aspect, the invention provides compositions which are suitable for pharmaceutical or diagnostic use. The compositions comprise compounds of formula provided above, in combination with a diagnostically or pharmaceutically acceptable carrier or excipient.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a pro-drug, which can be metabolically or chemically converted to the subject compound by the recipient host. A wide variety of pro-drug derivatives are known in the art such as those that rely on hydrolytic cleavage or oxidative activation of the prodrug.

The compositions may be provided in any convenient form, including tablets, capsules, lozenges, troches, hard candies, powders, sprays, creams, suppositories, etc. As such, the compositions, in pharmaceutically acceptable dosage units or in bulk, may be incorporated into a wide variety of containers. For example, dosage units may be included in a variety of containers including capsules, pills, etc.

Methods of Use

In yet another aspect, the present invention provides novel methods for the use of the foregoing compounds and compositions. In particular, the invention provides novel methods for treating or preventing viruses from the herpes family, preferably, cytomegalovirus infections. The methods typically involve administering to a patient an effective formulation of one or more of the subject compositions.

The invention provides methods of using the subject compounds and compositions to treat disease or provide medicinal prophylaxis to individuals who possess a compromised immune system or are expected to suffer immunosuppressed conditions, such as patients prior to undergoing immunosuppressive therapy in connection with organ transplantation or anticancer chemotherapy. These methods generally involve administering to the host an effective amount of the subject compounds or pharmaceutically acceptable compositions.

The compounds and compositions of the present invention may be advantageously combined and/or used in combination with other antiviral agents useful in the treatment and/or prevention of the viral infections described herein. The compounds and compositions may also be advantageously combined and/or used in combination with agents useful in the treatment and/or prevention of conditions often associated with the viral infections described herein, such as anti-HIV agents (described below), immunostimulatory agents (e.g., vaccines) or immunosuppressive agents (e.g., cyclosporin, FK-506 and rapamycin). In many instances, administration of the subject compounds or compositions in conjunction with these alternative agents enhances the efficacy of such agents. Accordingly, in some instances, the present compounds (salts), when combined or administered in combination with other antiviral or immunosuppressive agents, can be used in dosages which are less than the expected amounts when used alone, or less than the calculated amounts for combination therapy.

Suitable agents for combination therapy include those that are currently commercially available and those that are in development or will be developed. While antiviral agents may be particularly suitable for the treatment or prevention of a particular viral disorder(s), practitioners skilled in the art understand that such agents frequently are useful in treating a range of viral-related disorders. Exemplary agents useful in the treatment of CMV include acyclovir, cidofovir, ganciclovir, immunoglobulin (CMV-specific and unselected) and foscarnet. Other promising anti-CMV agents include a) the nucleoside/nucleotide analogs valaciclovir, valganciclovir, adefovir, dipivoxil and lobucavir; b) the antisense agents fomivirsen, GEM 132 (Hybridon), ISIS 13312 (ISIS); and c) other therapies like benzimidavir and sevirumab.

Exemplary anti-HIV agents include a) nucleoside analog reverse transcriptase inhibitors such as zidovudine (AZT), didanosine (ddI), zalcitabine (ddC, dideoxycytidine), stavudine (d4T), lamivudine (3TC), abacavir (1592U89), emtricitabine (FTC, Triangle Pharmaceuticals), BCH-10652 (BioChem Pharma) and the related nucleotide analogs (e.g., PMPA (Gilead Sciences)); b) non-nucleoside reverse transcriptase inhibitors such as nevirapine (NVP), delavirdine (DLV), efavirenz (DMP-266), emivirine (MKC-442), AG1549 (Agouron Pharmaceuticals; PNU142721 (Pharmacia),calanolide-A (Sarawak MediChem Pharmaceuticals); c) protease inhibitors such as saquinavir (SQV), ritonavir (RTV), indinavir (IDV), nelfinavir (NFV) saquinavir (SQV), amprenavir (APV), 232,632 (Bristol-Myers Squibb), tipranavir, DMP-450 (Triangle Pharmaceuticals), and lopinavir; d) immune stimulators such as interleukin 2 (Chiron), Reticulose® (Advance Viral Research Corporation), Multikine® (Cel-Sci Corporation), and HIV-1 immunogen (Immune Response Corporation). Other anti-HIV agents that may be used in combination with the compounds and compositions of the present invention include HIV integrase inhibitors (e.g., AR-177 (Aronex Pharmaceuticals)), fusion inhibitors (e.g., T-20 (Roche)) and antisense drugs (e.g., HGTV43 (Enzo Therapeutics)).

The compounds and compositions of the present invention may also be advantageously used as antiviral prophylactic treatment in combination with immunosuppressive protocols such as bone-marrow destruction (either by radiation or chemotherapy).

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

Preparation of the Compounds

Compounds of the present invention can be prepared following a synthesis route as outlined in FIG. 1 for the most preferred embodiments of the invention.

As shown in FIG. 1, (S)-2-Aminopropanol can be treated with benzaldehyde in ethanol followed by sodium borohydride to form the N-benzyl alcohol 2. Acylation of the amine with chloroacetyl chloride provides 3, which can be cyclized to 4 upon treatment with sodium hydride. Reduction of the amide carbonyl present in 4 with lithium aluminum hydride (LAH) provides the substituted morpholine 5. Hydrogenolysis of the N-benzyl group can be accomplished with hydrogen using a palladium on carbon catalyst to provide (S)-3-methylmorpholine 6.

Compound 6 can be combined with 2-chloro-4-hydroxy-6-methyl-5-nitropyrimidine (7), to provide compound 8. The hydroxy group present in 8 can then be converted to a chlorine upon treatment with POCl$_3$ to provide compound 9, which upon treatment with imidazole in ethanol yields the parent compound 1. Conversion of 1 to the various salts can then be accomplished upon treatment with an equivalent of a suitable sulfonic acid (illustrated in FIG. 1 as benzenesulfonic acid (PhSO$_3$H) and toluenesulfonic acid (p-MePhSO$_3$H)).

Analysis of Compounds

The subject compounds and compositions were demonstrated to have pharmacological activity in in vitro and in vivo assays, e.g., they are capable of specifically modulating a cellular physiology to reduce an associated pathology or provide or enhance a prophylaxis.

Certain preferred compounds and compositions are capable of specifically inhibiting or suppressing cytomegalovirus infection. For the assessment of activity against human CMV, a method was used which is similar to that described in Kohler, et al., *J. Virol.* 68:6589–6597 (1994). Briefly, a recombinant human cytomegalovirus (HCMV) was made containing a marker gene (luciferase) under the control of the promoter for the late 28 kDa viral structural phosphoprotein pp28. Human foreskin fibroblast (HFF) cells were infected with the recombinant HCMV virus (MOI 5), placed into 96-well plates, and cultured under standard cell-culture conditions. Compounds that were evaluated for anti-HCMV activity were added to the infected cells 20 hours later. The level of luciferase expression was measured 24 hours after treatment with the test compounds. The biological activity of the test compounds is described by their IC$_{50}$ values, the concentration of test compound that reduces recombinant HCMV late gene expression (represented by luciferase expression in the HFF culture) by 50% relative to control (vehicle-treated) infected cells. As an additional control, the cytotoxicity of test compounds on untreated HFF cells was also evaluated in cultured cell growth experiments.

The following examples are offered by way of illustration and not by way of limitation.

EXAMPLES

1H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz. Electron Ionization (EI) mass spectra were recorded on a Hewlett Packard 5989A mass spectrometer. Mass spectrometry results are reported as the ratio of mass over charge, followed by the relative abundance of each ion (in parentheses).

Example 1

This example illustrates the synthesis of two salts of Compound 1, according to the route shown in FIG. 1.

1.1 Preparation of 2-Chloro-4-hydroxy-6-methyl-5-nitropyrimidine (7):

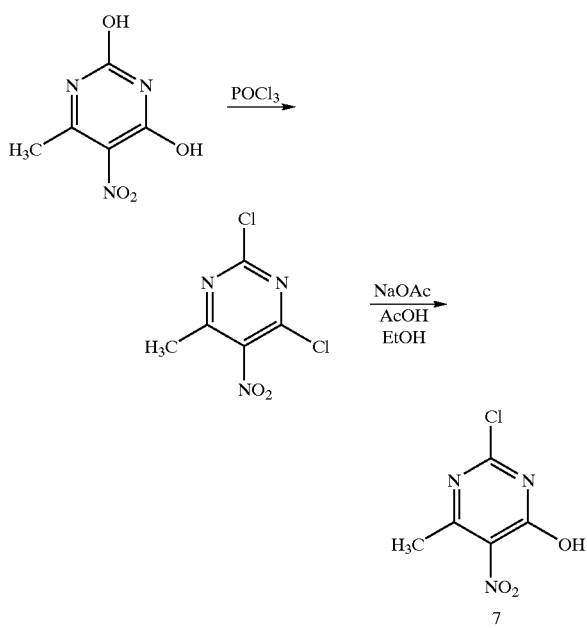

A 5 L flask was charged with tetraethylammonium chloride (590 g) which was then heated at 60° C. under vacuum for 22 h to remove any water. The flask was then charged with 3 L anhydrous CH$_3$CN, 2,4-dihydroxy-6-methyl-5-nitropyrimidine (295 g, 1.724 mol, 1.0 equiv), dimethylaniline (221 mL, 2.98 mol, 1.74 equiv), and 1 L POCl$_3$ (18.5 mol, 10.73 equiv). The flask was equipped with a condenser and the temperature was increased to 80° C. under N$_2$. After stirring for 29 h the hot black solution was poured onto 14 L ice and allowed to stir for 30 min while a yellow precipitate formed. The suspension was filtered, and the solid was washed 3×1.0 N HCl to give 247.3 g of dichloropyrimidine product. The aqueous solution from the filtration was extracted (3×CH$_2$Cl$_2$), dried (Na$_2$SO$_4$) and concentrated under reduced pressure. The resulting green oil was purified via flash chromatography (SiO$_2$, 1:1 hexanes:CH$_2$Cl$_2$), and the resulting light green solid was crystallized from hot hexanes. The crystals were washed with hexanes to give an additional 63.58 g of the yellow product. The combined yield of the dichloropyrimidine product was 310.88 g (1.495 mol, 87%).

The dichloropyrimidine prepared in the manner described above (150.0 g, 721 mmol) was dissolved in 3 L EtOH and cooled to 0° C. In a separate flask were combined 910 mL H$_2$O, 922 mL AcOH, and 90 g NaOAc. The aqueous solution was then added dropwise to the dichloride solution via dropping funnel over a period of 2 h. The solution was allowed to stir for 24 h by which time a light yellow precipitate was formed. The solid product was filtered off and the aqueous solution was set aside. The solid product was washed (3×200 mL EtOH) to give 70.3 g of the product as a fluffy light yellow solid. The aqueous solution was recooled to 0° C. followed by the addition of an additional 140 g dichloropyrimidine (673 mmol) and 84.5 g NaOAc. The resulting slurry was allowed to stir a further 24 h, at which time an additional 120.87 g of product was obtained via filtration as above. The remaining aqueous solution was allowed to stir at 0° C. for an additional 24 h, followed by filtration as above to give an additional 24.03 g product. Total product recovered was 215.2 g (1.135 mol, 79%) as a white solid: mp 242–244° C. (dec); IR(KBr) 3349, 1657, 1600, 1507, 1419, 1352, 1276, 1188, 1100, 998, 945, 799, 696, 624 cm−1; $^1$H NMR (CDCl$_3$, 400 MHz) δ 1.53 (s, 3H); ESI-MS m/z 212.0 (M+Na$^+$).

1.2 N-Benzyl-L-alaninol (2):

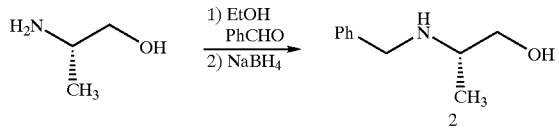

(S)-2-Aminopropanol (300 g, 3.994 mol, 1.0 equiv) was dissolved in 3.0 L of anhydrous EtOH in a 5 L three neck flask under N$_2$. Benzaldehyde (406.05 mL, 3.994 mol, 1.0 equiv) was added in one portion, and the slightly warm solution was allowed to stir for 2.5 h. The solution was then cooled to 0° C. in an ice bath, followed by the addition of 196.5 g NaBH$_4$ (5.194 mol, 1.3 equiv) over a period of 20 min. After stirring for 20 hours 521 mL H$_2$O was added via addition funnel over a period of 60 min. The resulting white slurry was then diluted with 3.0 L CH$_2$Cl$_2$ and stirred for an additional 5 h. The slurry was then filtered, and the solids were washed with three portions of CH$_2$Cl$_2$. The clear solution obtained from the filtration was then concentrated under reduced pressure to a volume of 800 mL. The solution was then diluted with 2 L H$_2$O, extracted (3×1.4 L CH$_2$Cl$_2$), dried (Na$_2$SO$_4$), and concentrated under reduced pressure to give a thick colorless oil, which quickly crystallized upon standing. The white solid was triturated with 1.0 L hexanes, filtered, and washed with hexanes (3×500 mL) to give the pure product as a white solid 648.65 g (3.926 mol, 98%): mp 39–40° C.; [α]$^{25}_D$=+38.5° (c=1.04, MeOH); IR (KBr) 3293, 3060, 3024, 2957, 2911, 2844, 1495, 1453, 1380, 1347, 1149, 1061, 965, 935, 873, 779, 746, 699, 611 cm−1; $^1$H NMR (CDCl$_3$, 400 MHz) δ 7.32 (m, 3H), 7.26 (m, 2H), 3.88 (d, J=12.8 Hz, 1H), 3.75 (d, J=12.8 Hz, 1H), 3.61 (dd, J=4.0, 10.6 Hz, 1H), 3.28 (dd, J=7.0, 10.6 Hz, 1H), 2.86 (ddddd, J=4.0, 6.6×3, 6.9 Hz, 1H), 1.78 (broad singlet, 2H), 1.10 (d, J=6.2 Hz, 3H); ESI-MS m/z 166.2 (100, M+H$^+$). Anal. Calcd for C$_{10}$H$_{15}$NO: C, 72.68; H, 9.15; N, 8.48. Found: C, 72.85; H, 9.06; N, 8.55.

1.3 5S-N-Benzylmorpholin-3-one (4):

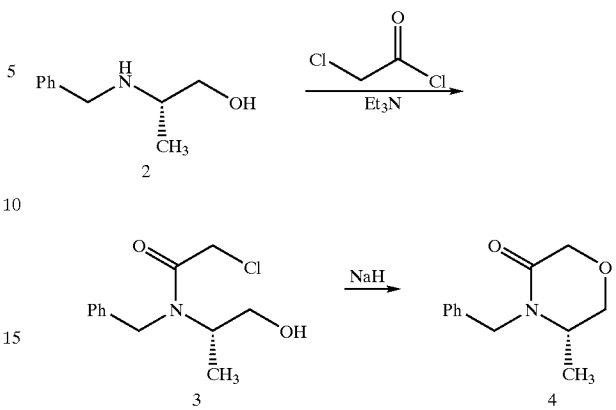

A 12 L three neck flask equipped with mechanical stirrer was charged with 648.65 g of N-benzyl-L-alaninol (3.926 mol, 1.0 equiv) and 4.0 L CH$_2$Cl$_2$. The solution was cooled to −10° C. in a methanol-ice bath followed by the addition of 547 mL Et$_3$N (3.926 mol, 1.0 equiv). Chloroacetyl chloride (312.2 mL, 3.926 mol, 1.0 equiv) was dissolved in 700 mL CH$_2$Cl$_2$, and the chloride solution was added dropwise via addition funnel resulting in a cloudy tan solution. The solution was stirred for 1 h, and was then diluted with 3 L H$_2$O. After stirring rapidly for 5 min, the layers were separated, and the water layer was extracted (3×700 mL CH$_2$Cl$_2$). The combined organics were washed (1×2 L H$_2$O), dried (500 g Na$_2$SO$_4$), and concentrated under reduced pressure to give amide 3 as a light red viscous oil, which was used directly in the cyclization step.

A 12 L flask equipped with a reflux condenser and mechanical stirrer was charged with 94.22 g NaH (3.92 mol, 1.0 equiv, Aldrich 95%) followed by 3.0 L anhydrous THF. The 2-chloroamide from above was dissolved in 3.0 L anhydrous THF and transferred via cannula to the NaH solution over a period of 25 min. The slurry was then slowly heated to 65° C. over 60 min. After stirring for 4.5 h at reflux, the sodium hydride was then quenched by the slow addition of 100 mL H$_2$O in 100 mL THF via dropping funnel. The heating mantle was then removed, and the reaction was allowed to cool down with stirring overnight. The majority of the THF was removed under reduced pressure, and the resulting slurry was diluted with 3 L CH$_2$Cl$_2$. The solid salts were filtered off, washed (3×CH$_2$Cl$_2$), and discarded. The resulting clear solution was diluted with 3 L H$_2$O, and extracted (5×700 mL CHCl$_3$). The combined organics were dried (Na$_2$SO$_4$), and concentrated under reduced pressure. Purification by flash chromatography (SiO$_2$, 100% CH$_2$Cl$_2$ to 5% MeOH/CH$_2$Cl$_2$) gave the product as a colorless oil 594.92 g (2.90 mol, 74%). [α]$^{25}_D$=−90° (c=1.0, MeOH); $^1$H NMR (CDCl$_3$, 400 MHz) δ 7.36–7.24 (m, 5H), 5.38 (d, J=15.4 Hz, 1H), 4.29 (d, J=16.5 Hz, 1H), 4.23 (d, J=16.8 Hz, 1H), 3.97 (d, J=15.0 Hz, 1H), 3.75 (dd, J=3.3, 11.7 Hz, 1 H), 3.64 (dd, J=3.3, 11.7 Hz, 1H), 3.56 (m, 1H), 1.28 (d, J=6.2 Hz, 3H); ESI-MS m/z 206.1 (100, M+H$^+$), 228.2 (45, M+Na$^+$). Anal. Calcd for C$_{12}$H$_{15}$NO$_2$: C, 70.22; H, 7.37; N, 6.82. Found: C, 70.16; H, 7.39; N, 6.83.

1.4 3S-N-Benzyl-3-methylmorpholine (5):

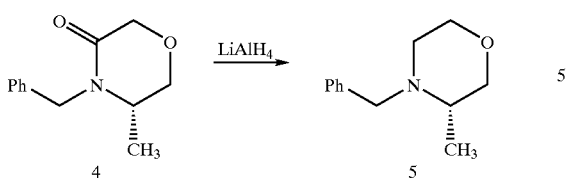

A 12 L three neck flask equipped with mechanical stirring device, heating mantle, and reflux condenser was charged with 220.14 g 95% LiAlH$_4$ (5.80 mol, 2.0 equiv) followed by 5.2 L anhydrous THF under N$_2$. The gray slurry was allowed to stir for 30 min. The N-Benzylmorpholin-3-one 4 (594.92 g, 2.90 mol, 1.0 equiv) was dissolved in 2 L THF, and added via addition funnel over the course of 3.5 h. The solution was then heated to reflux and allowed to stir at reflux for 19.5 h. The solution was then cooled to rt, followed by the careful addition of 220 mL H$_2$O in 665 mL THF via addition funnel over a period of 14 h. When all evolution of gas was stopped, 220 mL 15% NaOH was added, followed by 660 mL H$_2$O. The white slurry was then stirred for 56 h. The slurry was filtered through a fritted fimnel, and the solids were washed (5×600 mL Et$_2$O). The clear ethereal solution was then concentrated under reduced pressure to give the product as a colorless oil 509.04 g (2.66 mol, 92%). $[\alpha]^{25}_D$=+94.5° (c=1.10, MeOH); $^1$H NMR (CDCl$_3$, 400 MHz) δ 7.22–7.35 (m, 5H), 4.06 (d, J=13.2 Hz, 1H), 3.72 (m, 2H), 3.59 (ddd, J=2.6, 10.3, 11.3 Hz, 1H), 3.31 (dd, J=9.2, 11.3 Hz, 1H), 3.14 (d, J=13.5 Hz, 1H), 2.59 (ddd, J=2.6, 2.9, 12.1 Hz, 1H), 2.49 (m, 1H), 2.19 (ddd, J=3.3, 9.9, 12.1 Hz, 1H), 1.09 (d, J=6.2 Hz, 3H); ESI-MS m/z 192.2 (100, M+H$^+$). Anal. Calcd for C$_{12}$H$_{17}$NO: C, 75.35; H, 8.96; N, 7.32. Found: C, 75.48; H, 8.96; N, 7.23.

1.5 3S-3-Methylmorpholine (6):

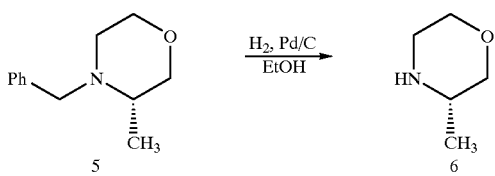

3S-N-Benzyl-3-methyl-morpholine (130.0 g, 680 mmol, 1.0 equiv) was dissolved in 200 mL EtOH and transferred to a Parr vessel. 10.0 g of Pd/C (10 wt % Pd) was added, and the Parr flask was sealed and subjected to hydrogenation on a Parr shaker at 62 PSI. Hydrogen pressure was adjusted periodically throughout the hydrogenation to maintain 60 PSI. After 44 h, the hydrogenation was stopped and the vessel was purged with nitrogen. The solution was filtered through a plug of celite, and the ethanolic solution was used directly in the next step.

1.6 2-(3S-3-Methylmorpholino)-4-hydroxy-6-methyl-5-nitropyrimidine (8).

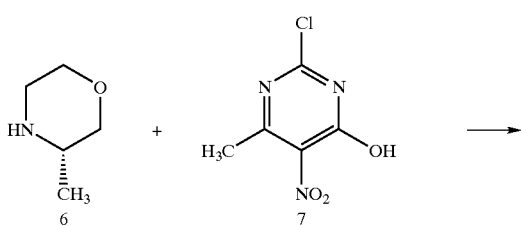

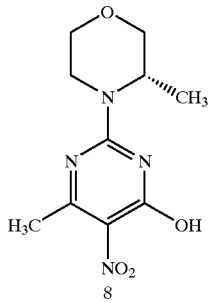

To the ethanolic solution of 3S-3-methylmorpholine 6 prepared above (~680 mmol, 3.2 equiv) in a 1 L flask under N$_2$ was added 2-chloro-4-hydroxy-6-methyl-5-nitropyrimidine (40.0 g, 211 mmol, 1.0 equiv) and 17.30 g anhydrous NaOAc (211 mmol, 1.0 equiv). The flask containing the light yellow slurry was equipped with a condenser and placed into a preheated oil bath at 80° C. After 24 h an additional 17.3 g NaOAc (211 mmol, 1.0 equiv) and 35.0 g potassium iodide (211 mmol, 1.0 equiv) was added to the bright orange slurry. After heating for an additional 21 h the flask was removed and the solution was allowed to cool to rt. The suspension was then filtered, and the solids were washed (3×50 mL EtOH). The combined ethanol solution was then concentrated to ~100 mL under reduced pressure and diluted with 0.5 N HCl until the pH was ~2. The solution was extracted (3×500 mL CH$_2$Cl$_2$), washed with 1.0 N HCl, dried (Na$_2$SO$_4$), and concentrated under reduced pressure to give the crude yellow solid. Purification via flash chromatography (SiO$_2$, 2–4% MeOH/CH$_2$Cl$_2$) gave the product as a yellow solid 40.86 g (160.8 mmol, 76%): mp 179–180° C.; $[\alpha]^{25}_D$=+135.1° (c=104, MeOH); IR (KBr) 3439, 3121, 2976, 2861, 1669, 1577, 1506, 1389, 1336, 1263, 1136, 1067, 982, 915, 846, 796 cm-1; $^1$H NMR (CDCl$_3$, 400 MHz) δ 7.37 (d, J=3.7 Hz, 1H), 4.72 (m, 1H), 4.45 (m, 1H), 4.02 (dd, J=3.7, 11.4 Hz, 1H), 3.80 (d, J=12.1 Hz, 1H), 3.67 (dd, J=2.9, 11.7 Hz, 1H), 3.53 (ddd, J=2.9, 11.7, 12.1 Hz, 1H), 3.36 (ddd, J=3.7, 12.8, 13.5 Hz, 1H), 2.58 (s, 3H), 1.59 (d, J=7.0 Hz, 3H); ESI-MS m/z 255.1 (100, M+H+). Anal. Calcd for C$_{10}$H$_{14}$N$_4$O$_4$: C, 47.24; H, 5.55; N, 22.04. Found: C, 47.14; H, 5.48; N, 22.15.

1.7 2-(3S-3-Methylmorpholino)-4-chloro-6-methyl-5-nitropyrimidine (9):

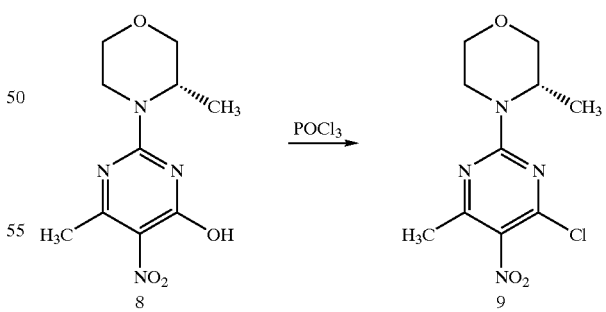

A 1 L flask containing the nitropyrimidine 8 prepared above (39.99 g, 157.4 mmol, 1.0 equiv) was charged with 250 mL POCl$_3$ under N$_2$. The flask was equipped with a condenser and placed in a preheated 80° C. bath with stirring. The slurry slowly dissolved over a period of 50 min, and the yellow solution was then removed from the bath, and POCl$_3$ was removed under reduced pressure in a rotary evaporator with a bath temperature of 60° C. The resulting yellow oil was purified via flash chromatography (SiO$_2$, 10 to 50% EtOAc/Hexanes) to give 40.24 g of the product (147.9 mmol, 94%) as a yellow oil. $[\alpha]^{25}_D$=+144.6° (c=1.03, MeOH); $^1$H NMR (CDCl$_3$, 400 MHz) δ 4.76 (m, 1H), 4.44 (m, 1H), 3.99 (dd, J=4.0, 11.7 Hz, 1H), 3.78 (d, J=11.7 Hz, 1H), 3.65 (dd, J=3.3, 11.7 Hz, 1H), 3.51 (ddd, J=2.9, 11.7, 12.4 Hz, 1H), 3.32 (ddd, J=4.0, 12.4, 13.9 Hz, 1H), 2.45 (s, 3H), 1.34 (d, J=7.0 Hz, 3H); ESI-MS m/z 273.0 (100, M+H+).

1.8 2-(3S-3-Methylmorpholino)-4-(imidazol-1-yl)-6-methyl-5-nitropyrimidine (1)

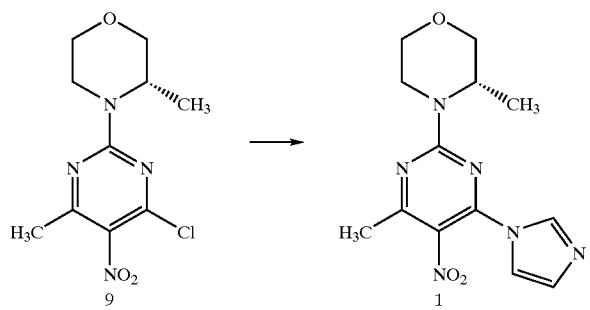

The chloropyrimidine 9 prepared above (40.04 g, 147.2 mmol, 1.0 equiv) was dissolved in 300 mL anhydrous EtOH followed by the addition of 30.07 g imidazole (441.6 mmol, 3.0 equiv) under N$_2$. The flask was equipped with a condenser and placed in a preheated 80° C. bath with magnetic stirring. After stirring for 75 min the solution was cooled to rt and concentrated under reduced pressure. Purification via flash chromatography (SiO$_2$, 2–4% MeOH/CH$_2$Cl$_2$) gave the product as a yellow oil. Upon standing the oil crystallized to give a yellow solid which was titurated with hexanes, filtered, and washed (3×hexanes) to give 40.53 g (133.3 mmol, 91%) of the product as yellow crystals: mp=74–75° C.; $[\alpha]^{25}_D$=+152.6° (c=1.03, MeOH); IR (KBr) 3116, 2972, 2855, 1586, 1482, 1443, 1329, 1315, 1239, 1205, 1129, 1074, 1007, 897, 844, 773, 739, 650 cm−1; $^1$H NMR (CDCl$_3$, 400 MHz) δ 8.10 (s, 1H), 7.21 (m, 1H), 7.17 (m, 1H), 4.80 (m, 1H), 4.48 (m, 1H), 4.02 (dd, J=3.7, 11.7 Hz, 1H), 3.80 (d, J=11.7 Hz, 1H), 3.68 (dd, J=3.3, 11.7 Hz, 1H), 3.52 (ddd, J=2.9, 11.7, 12.1 Hz, 1H), 3.36 (ddd, J=3.7, 12.9, 13.5 Hz, 1H), 2.53 (s, 3H), 1.38 (d, J=7.0 Hz, 3H); ESI-MS m/z 305.1 (100, M+H+). Anal. Found for C$_{13}$H$_{16}$N$_6$O$_3$: C, 51.31; H, 5.30; N, 27.62. Found: C, 51.47; H, 5.30; N, 27.79.

1.9 Preparation of Compound 1.PhSO3 Salt (2-(3S-3-Methylmorpholino)-4-(imidazol-1-yl)-6-Methyl-5-nitropyrimidine Benzenesulfonate):

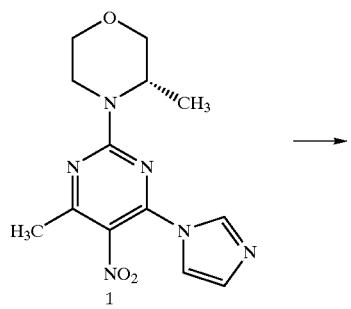

A 250 mL flask was charged with 1 (39.88 g, 131.1 mmol, 1.0 equiv) and 100 mL EtOH under N$_2$. The suspension was heated to 50° C. until everything dissolved. Benzenesulfonic acid hydrate (20.81 g, 131.1 mmol, 1.0 equiv) was added via spatula, and additional EtOH was used to wash the all of the solids into the flask (5 mL). Hexane (20 mL) was added to the solution, which was then stirred rapidly for 5 min. Crystals began to form within the first 5 min after stirring was stopped, and the flask was allowed to cool to rt overnight. The crystals which formed overnight were filtered and washed (5×50 mL EtOH) to give the product besilate salt 51.988 g (112.4 mmol, 86%): Yellow crystals mp 184.5° C.; $[\alpha]^{25}_D$+115.6° (c 1.00, MeOH); IR (KBr) 3442, 3129, 2985, 2862, 1597, 1546, 1529, 1490, 1443, 1317, 1231, 1182, 1123, 1072, 1014, 892, 846, 786, 727, 612, 564 cm−1; $^1$H NMR (400 MHz, CD$_3$OD) δ 9.52 (s, 1H), 7.93 (s, 1H), 7.81 (m, 2H), 7.42 (s, 1H), 7.44–7.37 (m, 3H), 4.94 (m, 0.5H), 4.74 (m, 0.5H), 4.62 (m, 0.5 H), 4.62 (m, 0.5H), 4.01 (m, 1H), 3.79 (m, 1H), 3.67 (dd, J=3.3, 11.8 Hz, 1H), 3.53 (ddd, J=2.8, 11.3, 12.3 Hz, 1H), 3.42 (ddd, J=3.6, 12.8, 13.2 Hz, 1H), 2.68 (s, 3H), 1.36 (d, J=6.9 Hz, 3H). Anal. Calcd for C$_{13}$H$_{16}$N$_6$O$_3$.C$_6$H$_6$O$_3$S: C, 49.34; H, 4.79; N, 18.17; S, 6.92. Found: C, 49.30; H, 4.75; N, 18.22; S, 6.97.

1.10 Preparation of Compound 1.p-MePhSO3 Salt (2-(3S-3-Methylmorpholino)-4-(imidazol-1-yl)-6-methyl-5-nitropyrimidine p-toluenesulfonate):

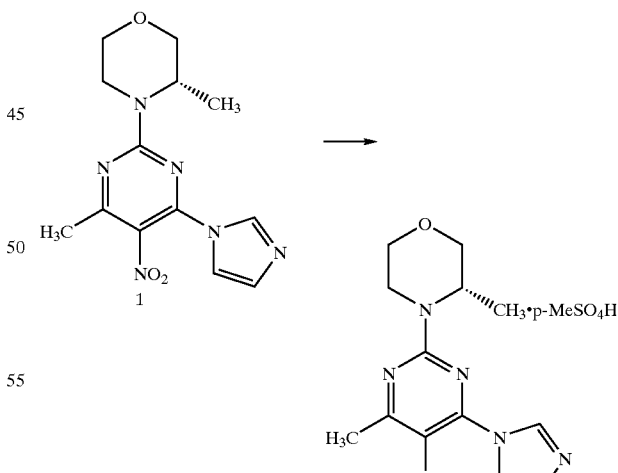

A 25 mL flask was charged with 822 mg 1 (2.70 mmol, 1.0 equiv) and 3 mL CH$_2$Cl$_2$, followed by the addition of 514 mg (2.70 mmol, 1.0 equiv) p-toluenesulfonic acid mono hydrate. 1.5 mL hexanes was added and the clear solution was allowed to sit overnight. The solution was then concentrated under reduced pressure and taken up in 3 mL EtOAc whereupon a yellow solid precipitated out. The yellow solid was filtered, and washed (3×1:1 hexanes:EtOAc) to give 1.202 g. The yellow solid was recrystallized from 5:1 CHCl$_3$:hexanes to give 1.078 g of product (2.26 mmol, 84%) salt after filtration and washing (2×1:1 CHCl$_3$:hexanes): mp 168–169° C.; [α]$^{25}_D$=+104.9° (c=1.05, MeOH); IR (KBr) 3128, 2981, 2858, 1595, 1544, 1526, 1442, 1317, 1227, 1184, 1123, 1030, 1007, 683, 562 cm–1; $^1$H NMR (400 MHz, CD$_3$OD) δ 9.53 (s, 1H), 7.94 (m, 1H), 7.74 (m, 1H), 7.69 (d, J=8.4 Hz, 2H), 7.21 (d, J=8.4 Hz, 2H), 4.94 (m, 0.5 H), 4.75 (m, 0.5H), 4.62 (m, 0.5H), 4.41 (m, 0.5H), 3.99 (m, 1H), 3.80 (m, 1H), 3.67 (dd, J=2.9, 11.7Hz, 1H), 3.53 (ddd, J=2.6, 11.7, 12.1 Hz, 1H), 3.41 (ddd, J=3.7, 12.5, 13.6 Hz, 1H), 2.68 (s, 3H), 2.36 (s, 3H), 1.37 (d, J=7.0 Hz, 1H). Anal. Calcd for C$_{13}$H$_{16}$N$_6$O$_6$·C$_7$H$_8$O$_3$S: C, 50.41; H, 5.08; N, 17.64; S, 6.73. Found: C, 49.88; H, 4.75; N, 18.23; S, 6.91.

Example 2

This example illustrates the initial physical properties of the arylsulfonic acid salts of compound 1, relative to other salts of compound 1.

TABLE 1

Acid Selection.

| Acid | pKa | Solvent | Result |
|---|---|---|---|
| Hydrobromic | –9.0 | EtOH | Decomposition |
| Hydrochloric | –6.1 | CH$_3$CN | Decomposition |
| Hydrochloric | –6.1 | CHCl$_3$ | Decomposition |
| Hydrochloric | –6.1 | Et$_2$O | Decomposition |
| Hydrochloric | –6.1 | EtOAc | Decomposition |
| Hydrochloric | –6.1 | IPA | Decomposition |
| Hydrochloric | –6.1 | MeOH | Decomposition |
| Sulfuric | –3.0 | EtOH | Decomposition |
| Nitric | –1.4 | EtOH | Decomposition |
| Methanesulfonic | –1.2 | CH$_2$Cl$_2$ | Decomposition |
| Methanesulfonic | –1.2 | Et$_2$O | Decomposition |
| Methanesulfonic | –1.2 | EtOAc | Decomposition |
| Methanesulfonic | –1.2 | EtOAc/CH$_2$Cl$_2$ | Decomposition |
| Methanesulfonic | –1.2 | EtOAc/hexanes | Decomposition |
| Benzenesulfonic | 1.6 | CH$_2$Cl$_2$/hexanes | Yellow crystals |
| Benzenesulfonic | 1.6 | CH$_3$CN | Yellow crystals |
| Benzenesulfonic | 1.6 | CHCl$_3$/hexanes | Yellow crystals |
| Benzenesulfonic | 1.6 | EtOAc/MeOH | Yellow crystals |
| Benzenesulfonic | 1.6 | EtOH | Yellow crystals |
| Benzenesulfonic | 1.6 | EtOH/hexanes | Yellow crystals |
| Toluenesulfonic | 1.7 | CHCl$_3$/hexanes | Yellow crystals |
| Toluenesulfonic | 1.7 | EtOAc | Yellow crystals |
| Maleic | 2.0, 6.3 | Et$_2$O | No salt formed |
| Maleic | 2.0, 6.3 | EtOAc | No salt formed |
| D-Tartaric | 2.9 | EtOAc | No salt formed |
| D-Tartaric | 2.9 | MeOH | No salt formed |
| L-Tartaric | 2.9 | Et$_2$O | No salt formed |
| L-Tartaric | 2.9 | EtOAc | No salt formed |
| L-Tartaric | 2.9 | EtOH | No salt formed |
| L-Tartaric | 2.9 | MeOH | No salt formed |
| Salicylic | 2.98 | Et$_2$O | No salt formed |
| Salicylic | 2.98 | EtOAc | No salt formed |
| Fumaric | 3.0, 4.4 | EtOAc/MeOH | No salt formed |
| Citric | 3.1 | Et$_2$O | No salt formed |
| Citric | 3.1 | EtOAc | No salt formed |
| Citric | 3.1 | EtOAc/MeOH | No salt formed |
| R-Mandelic | 3.4 | Et$_2$O | No salt formed |
| R-Mandelic | 3.4 | EtOAc | No salt formed |
| S-Mandelic | 3.4 | Et$_2$O | No salt formed |
| Formic | 3.75 | EtOH | No salt formed |
| 3-Hydroxy-benzoic | 4.1, 9.9 | EtOAc | No salt formed |
| Benzoic | 4.2 | Et$_2$O | No salt formed |
| Benzoic | 4.2 | EtOAc | No salt formed |
| Succinamic | 4.4 | EtOAc | No salt formed |
| Succinamic | 4.4 | EtOAc/MeOH | No salt formed |
| Acetic | 4.8 | Et$_2$O | No salt formed |

Example 3

This example illustrates additional physical evaluation of the aryl sulfonic acid salts of compound 1.

3.1 Comparison of Salts with Free Base of Compound 1.

The besilate and tosylate salts represent improvement over the free base in solubility as described in Table 2 below. The increase in solubility represents a significant advantage over the free base for formulations that are suitable for therapeutic administration.

| Property | Compound 1 | Tosylate Salt | Besilate Salt |
|---|---|---|---|
| Melting point | 74–75° C. | 168–169° C. | 184–185° C. |
| Aqueous Solubility (mg/mL) | 1.68 | 36 | 44 |

3.2 Thermal Stability of Salts at 45° C.

The besilate and tosylate salts also demonstrated surprising stability at 45° C., over a period of from 8 hours to at least 1632 hours.

| Time (hours) | Tosylate Salt (purity %, HPLC) | Besilate Salt (purity %, HPLC) |
|---|---|---|
| 8 | 100 | 100 |
| 24 | 100 | 100 |
| 48 | 100 | 100 |
| 72 | 100 | 100 |
| 170 | 100 | 100 |
| 250 | 100 | 100 |
| 1632 | 100 | 100 |

3.3 Light Stability of Salts

The besilate and tosylate salts also demonstrated surprising stability when exposed to ambient light and window glass filtered sunlight, over a period of from 24 hours to 1560 hours.

| Time (hours) | Tosylate Salt (purity %, HPLC) | Besilate Salt (purity %, HPLC) |
|---|---|---|
| 24 | 100 | 100 |
| 48 | 100 | 100 |
| 216 | 97.6 | 97.3 |
| 1560 | 86.6 | 93.1 |

3.4 Aqueous Stability of Salts

The besilate and tosylate salts also demonstrated stability in deionized water. The tosylate salts was evaluated at a concentration of 4.7 mg/mL and the besilate salt was evaluated at a concentration of 3.2 mg/mL. Stability was monitored via HPLC using UV detection at 254.4 nm.

| Time (hours) | Tosylate Salt (purity %, HPLC) | Besilate Salt (purity %, HPLC) |
|---|---|---|
| 48 | 100 | 100 |
| 147 | 100 | 100 |
| 171 | 97.3 | 97.4 |
| 201 | 93.1 | 91.7 |
| 216 | 92.8 | 91.7 |
| 1560 | 64.6 | 61.4 |

3.5 Crystal Forms of the Salts

The crystal forms of the benzenesulfonate and toluenesulfonate salts represent a unique physical form of these two entities and may be defined by their X-ray powder diffraction spectra as described below:

Benzenesulfonate (besilate): Two-theta diffraction angles in degrees (relative intensities); 15.32 (100), 23.04 (43), 24.5 (12), 30.84 (10).

Tosylate: Two-theta diffraction angles in degrees (relative intensities); 7.47 (13), 9.54 (81), 10.69 (30), 11.93 (80), 13.85 (47), 14.14 (59), 15.09 (100), (11), 19.15 (91), 19.45 (38), 20.67 (83), 22.29 (37), 23.85 (65), 24.41 (65), 26.28 (19), 26.80 (20), 27.71 (15.5), 29.07 (8), 29.78 (13), 34.00 (8).

3.6 Oral Bioavailability of Compound 1 (Free Base, Besilate Salt and Tosylate Salt).

Figure 2:
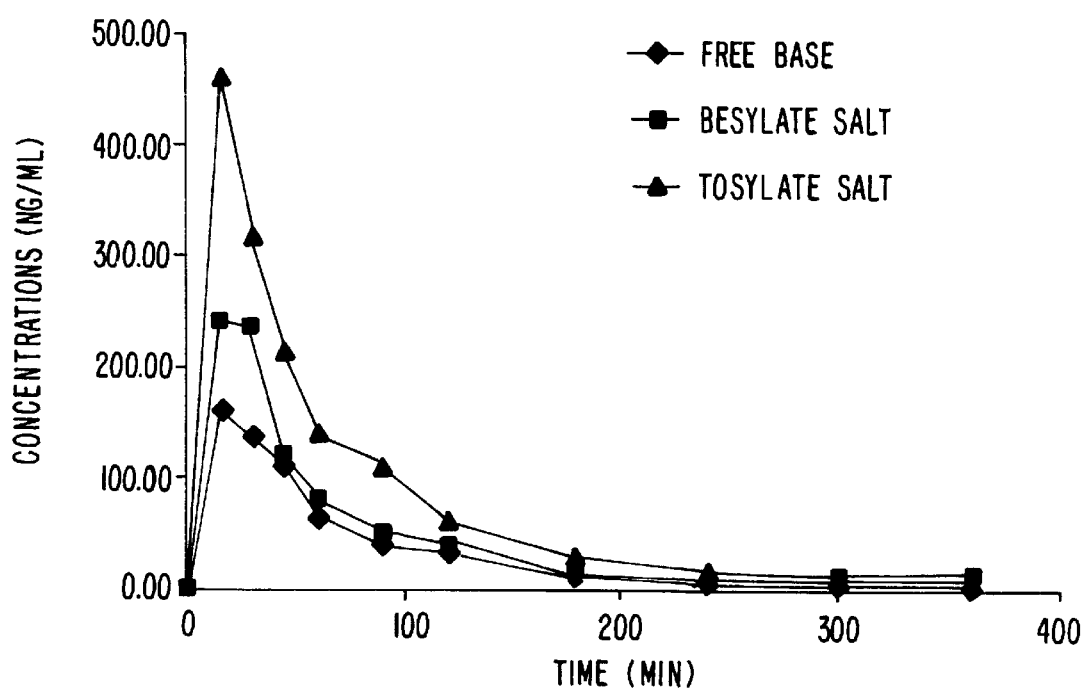
FIG. 2 is a graph illustrating the increased oral bioavailability of compound 1, when administered as an arylsulfonic acid salt (compared to the free base of compound 1).

Compound 1 was administered to rats orally (10 mg/kg) as the free base, the tosylate salt and the besilate salt. At the indicated time points (see FIG. 2), plasma samples were evaluated for the presence of compound 1. Relative bioavailability of the salts was calculated based on an availability of 100% for the free base. As FIG. 2 indicates, the besilate salt provided a bioavailability of 155% while the tosylate salt provided a bioavailability of 242%.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

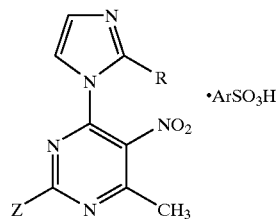

wherein

R is a member selected from the group consisting of hydrogen, methyl and ethyl;

Z is a substituted or unsubstituted 4-morpholinyl; and

Ar is a member selected from the group consisting of substituted or unsubstituted phenyl and substituted or unsubstituted naphthyl.

2. A compound in accordance with claim 1, wherein R is hydrogen, Z is a substituted or unsubstituted 4-morpholinyl, and Ar is substituted or unsubstituted phenyl.

3. A compound in accordance with claim 2, wherein Z is a mono-substituted 4-morpholinyl group, said substituent being selected from the group consisting of $(C_1–C_4)$alkyl.

4. A compound in accordance with claim 3, wherein Ar is phenyl or tolyl.

5. A compound in accordance with claim 4, said compound selected from the group consisting of

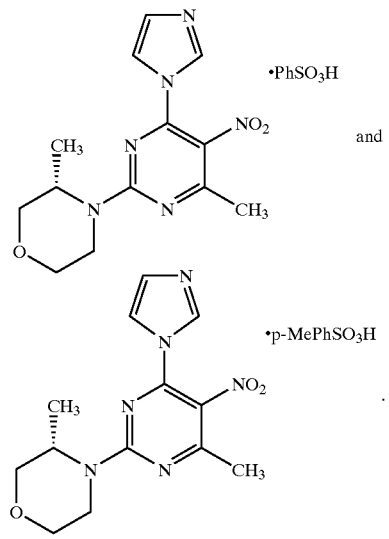

6. A composition comprising a pharmaceutically acceptable excipient and a compound having the formula:

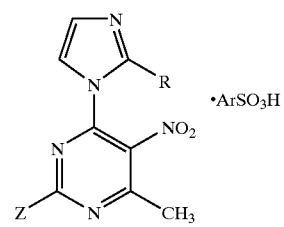

wherein

R is a member selected from the group consisting of hydrogen, methyl and ethyl;

Z is a substituted or unsubstituted 4-morpholinyl; and

Ar is a member selected from the group consisting of substituted or unsubstituted phenyl and substituted or unsubstituted naphthyl.

7. A composition in accordance with claim 6, wherein R is hydrogen and Z is a substituted or unsubstituted 4-morpholinyl.

8. A composition in accordance with claim 6, wherein R is hydrogen, Z is a substituted or unsubstituted 4-morpholinyl, and Ar is substituted or unsubstituted phenyl.

9. A composition in accordance with claim 8, wherein Z is a mono-substituted 4-morpholinyl group, said substituent being selected from the group consisting of $(C_1–C_4)$alkyl.

10. A composition in accordance with claim 9, wherein Ar is phenyl or tolyl.

11. A composition in accordance with claim 10, said compound selected from the group consisting of

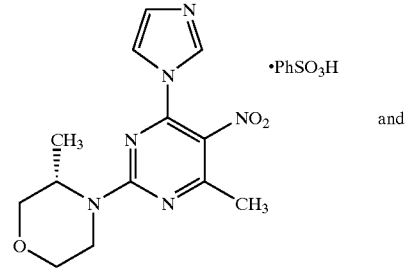

-continued

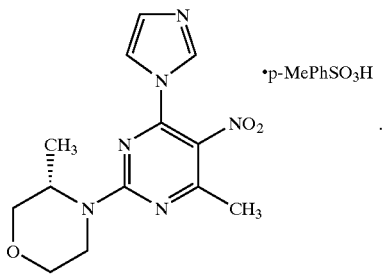

12. A method for treating a viral infection in a mammal, comprising administering to said mammal a therapeutically effective amount of a compound having the formula:

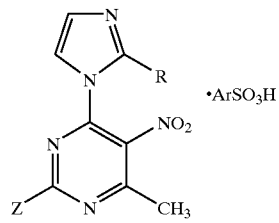

wherein
R is a member selected from the group consisting of hydrogen, methyl and ethyl;
Z is a substituted or unsubstituted 4-morpholinyl; and
Ar is a member selected from the group consisting of substituted or unsubstituted phenyl and substituted or unsubstituted naphthyl.

13. A method in accordance with claim 12, wherein R is hydrogen, Z is substituted or unsubstituted 4-morpholinyl, and Ar is substituted or unsubstituted phenyl.

14. A method in accordance with claim 13, wherein Z is a mono-substituted 4-morpholinyl group, said substituent being selected from the group consisting of $(C_1-C_4)$alkyl.

15. A method in accordance with claim 14, said compound selected from the group consisting of

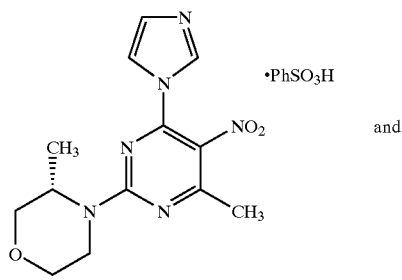

and

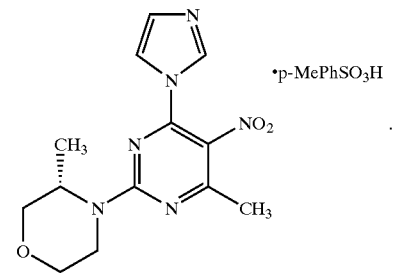

16. A method in accordance with claim 15, wherein said mammal is one with a compromised immune system.

17. A method in accordance with claim 15, wherein said administering is topical.

18. A method in accordance with claim 15, wherein said administering is oral.

19. A method in accordance with claim 15, wherein said viral infection produces a disease selected from the group consisting of CMV-retinitis, CMV-mononucleosis, CMV-pneumonitis and CMV-hepatitis.

20. A method in accordance with claim 15, wherein said administering is parenteral.

21. A method in accordance with claim 15, wherein said compound in administered in combination with an agent selected from the group consisting of ganciclovir, acyclovir, foscarnet and cidofovir.

22. A method in accordance with claim 21, wherein said compound and said agent are each administered in an amount of from 1/100 to less than ½ of their normal individual therapeutic doses.

23. A method in accordance with claim 22, wherein said compound and said agent are each administered in an amount of from 1/10 to about ¼ of their normal individual therapeutic doses.

24. A compound in accordance with claim 5, wherein said compound is

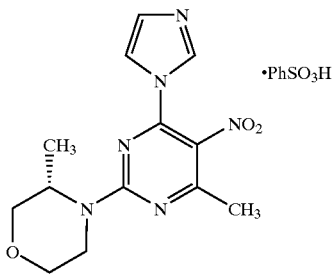

25. A composition in accordance with claim 11, wherein said compound is

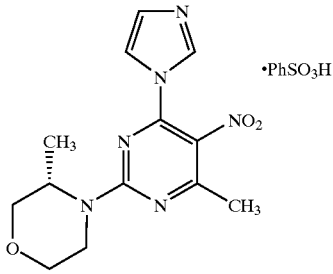

26. A method in accordance with claim 15, wherein said compound is

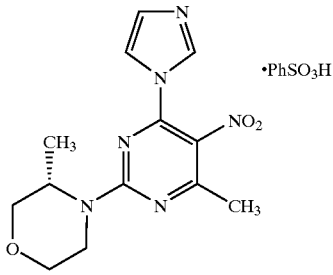

27. A method in accordance with claim 15, wherein said viral infection is a herpesvirus infection.

28. A method in accordance with claim 15, wherein said viral infection is a cytomegalovirus infection.

* * * * *